US009656939B2

(12) United States Patent
Hallinan et al.

(10) Patent No.: US 9,656,939 B2
(45) Date of Patent: May 23, 2017

(54) ACETIC ACID PROCESS

(71) Applicant: LyondellBasell Acetyls, LLC, Houston, TX (US)

(72) Inventors: Noel C. Hallinan, Loveland, OH (US); Jenny M. Oran Osment, Humble, TX (US); David L. Ramage, Friendswood, TX (US)

(73) Assignee: LyondellBasell Acetyls, LLC, Houston, TX (US)

( * ) Notice: Subject to any disclaimer, the term of this patent is extended or adjusted under 35 U.S.C. 154(b) by 0 days.

(21) Appl. No.: 15/062,756

(22) Filed: Mar. 7, 2016

(65) Prior Publication Data

US 2016/0264502 A1 Sep. 15, 2016

Related U.S. Application Data

(60) Provisional application No. 62/130,369, filed on Mar. 9, 2015.

(51) Int. Cl.
*C07C 51/12* (2006.01)
*G01N 21/65* (2006.01)
*G01N 21/3577* (2014.01)
*G01N 21/35* (2014.01)

(52) U.S. Cl.
CPC ......... *C07C 51/12* (2013.01); *G01N 21/3577* (2013.01); *G01N 21/65* (2013.01); *G01N 2021/3595* (2013.01)

(58) Field of Classification Search
CPC .... C07C 51/12; G01N 21/3577; G01N 21/65; G01N 2021/3595
USPC ........................................................ 562/519
See application file for complete search history.

(56) References Cited

U.S. PATENT DOCUMENTS

| 6,362,366 B1* | 3/2002 | Hallinan ............. B01J 19/0006 562/517 |
| 2012/0095259 A1 | 4/2012 | Salisbury et al. |
| 2012/0220801 A1 | 8/2012 | Salisbury et al. |

OTHER PUBLICATIONS

Villanova ("Raman Spectroscopy" p. 1-37, Feb. 11, 2013, downloaded from <http://www.chemistry.uoc.gr/courses/suprachem/spectroscopies/%201%20Raman/1-Raman%20spectroscopy%202013.ppt>).*
PCT/US2016/021179 International Search Report and Written Opinion Mailed Jun. 20, 2016.

* cited by examiner

*Primary Examiner* — Jafar Parsa
*Assistant Examiner* — Amy C Bonaparte

(57) ABSTRACT

The present disclosure provides for a method for measuring the concentration of one or more components in the reactor or a separation unit of an acetic acid process by both infrared and Raman spectroscopic analyses. In some embodiments, the conditions in the reactor or in any subsequent step of the acetic acid production process are adjusted in response to the measured concentration of one or more components.

10 Claims, 2 Drawing Sheets

ACETIC ACID PROCESS

CROSS-REFERENCE TO RELATED APPLICATIONS

This application claims the benefit of priority to U.S. Provisional Application No. 62/130,369, filed on Mar. 9, 2015, which is incorporated herein by reference in its entirety.

FIELD OF THE INVENTION

The present disclosure relates to an acetic acid preparation process. In particular, the present disclosure relates to controlling an acetic acid production process by: (a) using Raman spectroscopy to measure the concentration of components in a product stream; and (b) correlating Raman spectroscopy measurements with online Fourier Transform Infrared (FTIR) spectroscopy measurements of components in the product stream.

BACKGROUND OF THE INVENTION

Acetic acid is commercially produced from methanol and carbon monoxide by methanol carbonylation in the presence of water. The process may further contain methyl acetate as a co-feed. As an alternative to methyl acetate as a co-feed, the reaction can take place in the presence of a mixture of methyl acetate and methanol from byproduct streams of the hydrolysis/methanolysis of polyvinyl acetate. Various techniques can be used to determine the components of the reaction mixture and to modify the process.

SUMMARY OF THE INVENTION

In some embodiments, the present disclosure provides a method for measuring the concentration of one or more components in a reactor or a separation unit of the acetic acid process by both infrared and Raman spectroscopic analyses and adjusting the conditions in the reactor or in any subsequent step of the acetic acid production process in response to the measured concentration.

In another general embodiment, the present disclosure provides for a method for producing acetic acid comprising:
 (A) reacting, in a carbonylation reactor and the presence of a carbonylation catalyst, ingredients comprising:
  (i) methanol,
  (ii) carbon monoxide, and
  (iii) water,
  to produce a reactor mixture;
 (B) measuring the concentration of a reference component and a second component in the reactor mixture by both infrared and Raman spectroscopic analyses;
 (C) determining the ratio (alternatively referred to as the "Adjustment Ratio") of the concentration of the reference component as measured by infrared spectroscopy to the concentration as measured by Raman spectroscopy;
 (D) calculating the adjusted value ("Adjusted Value") for the second component by multiplying the concentration of the second component as measured by Raman spectroscopy by the Adjustment Ratio; and
 (E) modifying a process condition in the carbonylation reactor or a separation unit, based upon the Adjusted Value.

BRIEF DESCRIPTION OF THE DRAWINGS

Further details will be apparent from the following detailed description, with reference to the enclosed drawings, in which.

DETAILED DESCRIPTION OF THE INVENTION

Figure 1:
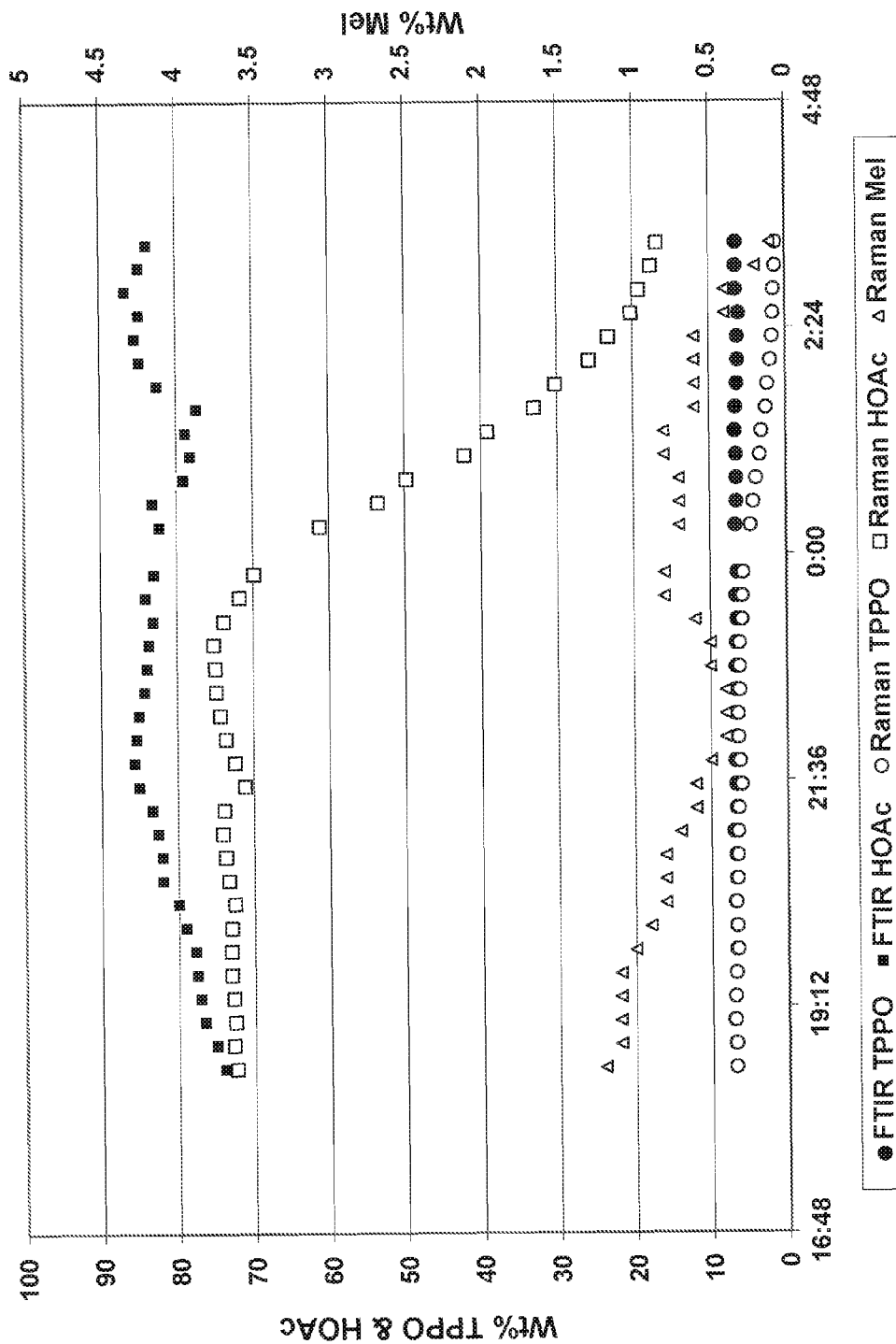
FIG. 1 is a graph showing time-lapse measurements of certain components in a methyl carbonylation process.

The present disclosure now will be described more fully hereinafter. However, this technology may be embodied in many different forms and should not be construed as limited to the embodiments set forth herein; rather, these embodiments are provided so that this disclosure will satisfy applicable legal requirements. As such, it will be apparent to those skilled in the art that the embodiments may incorporate changes and modifications without departing from the general scope of the disclosure. It is intended to include all such modifications and alterations in so far as they come within the scope of the appended claims or the equivalents thereof.

As used in this specification and the claims, the singular forms "a," "an," and "the" include plural referents unless the context clearly dictates otherwise.

As used in this specification and the claims, the terms "comprising," "containing," or "including" mean that at least the named compound, element, material, particle, method step, etc., is present in the composition, the article, or the method, but does not exclude the presence of other compounds, elements, materials, particles, method steps, etc., even if the other such compounds, elements, materials, particles, method steps, etc., have the same function as that which is named, unless expressly excluded in the claims. It is also to be understood that the mention of one or more method steps does not preclude the presence of additional method steps before or after the combined recited steps or intervening method steps between those steps expressly identified.

Moreover, it is also to be understood that the lettering of process steps or ingredients is a convenient means for identifying discrete activities or ingredients and the recited lettering can be arranged in any sequence, unless expressly indicated.

For the purpose of the present description and of the claims which follow, except where otherwise indicated, all numbers expressing amounts, quantities, percentages, and so forth, are to be understood as being modified in all instances by the term "about". Also, all ranges include any combination of the maximum and minimum points disclosed and include any intermediate ranges therein, which may or may not be specifically enumerated herein.

Acetic acid is commercially produced from methanol and carbon monoxide by methanol carbonylation in the presence of water. The process may further contain methyl acetate as a co-feed. As an alternative to methyl acetate as a co-feed, the reaction can take place in the presence of a mixture of methyl acetate and methanol from byproduct streams of the hydrolysis/methanolysis of polyvinyl acetate. Additionally, methyl acetate may be generated during the process. Such carbonylation processes can use catalyst systems based on (a) rhodium or (b) iridium, with or without a catalyst stabilizer or a catalyst promoter.

When the catalyst is based on rhodium, the catalyst can be rhodium metal or a rhodium compound. The rhodium compounds can be selected from the group consisting of rhodium salts, rhodium oxides, rhodium acetates, organo-rhodium compounds, coordination compounds of rhodium and mixtures thereof. Specific examples of rhodium compounds include $Rh_2(CO)_4I_2$, $Rh_2(CO)_4Br_2$, $Rh_2(CO)_4Cl_2$, $Rh(CH_3CO_2)_2$, $Rh(CH_3CO_2)_3$ and $[H]Rh(CO)_2I_2$.

When the catalyst is based on iridium, the catalyst can be iridium metal or an iridium compound. The iridium compounds can be selected from the group consisting of iridium salts, iridium oxides, iridium acetates, iridium oxalates, iridium acetoacetates, coordination compounds of iridium and mixtures thereof. Specific examples of iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3 \cdot 4H_2O$, $IrBr_3 \cdot 4H_2O$, $Ir_3(CO)_{12}$, $Ir_2O_3$, $IrO_2$, $Ir(acac)(CO)_2$, $Ir(acac)_3$, $Ir(Ac)_3$, $[Ir_3O(OAc)_6(H_2O)_3][OAc]$ and $H_2[IrCl_6]$.

In general, there are two types of catalyst stabilizers. The first type of catalyst stabilizer is metal iodide salt such as lithium iodide. The second type of catalyst stabilizer is a non-salt stabilizer, including pentavalent Group VA oxides such as phosphine oxides.

An example of a catalyst promoter is methyl iodide. Methyl iodide may be added directly to the process or generated by adding hydrogen iodide to the process.

As previously noted, methanol and carbon monoxide are fed to the carbonylation reactor. It is believed that the methanol does not react directly with the carbon monoxide to form acetic acid. Instead, it is converted to methyl iodide by the hydrogen iodide present in the acetic reactor and then reacted with carbon monoxide and water to give acetic acid and regenerate the hydrogen iodide.

The carbonylation reaction can be performed at a temperature within the range of about 150 degrees Celsius (° C.) to about 250° C. and under a pressure within the range of about 200 psig (1380 kPa) to about 2,000 psig (13,800 kPa).

After the carbonylation reaction, the reaction mixture is passed downstream to separation units. Separations unit may be defined herein as a vessel or step in an acetic acid process which separates a feed stream into two or more separate exit streams where the two exit streams differ from one another in some aspect. The separation can be based on methods such as separation by physical characteristics (e.g., density, volatility, boiling point, phase, absorbance, and adsorbance) and other characteristics used for separating chemical components.

The separation units can include, but are not limited to, a flash tank, a light ends distillation column, a decanter, a drying column, and a heavy ends distillation column.

In a flash tank, the acetic acid product stream is withdrawn from the reactor and separated into (a) a liquid fraction containing the catalyst and the catalyst stabilizer and (b) a vapor fraction containing the acetic acid product, the reactants, water, methyl iodide, and impurities generated during the carbonylation reaction including acetaldehyde. The liquid fraction can be recycled to the carbonylation reactor. The vapor fraction is then passed to a distillation column.

In a light ends distillation column, the vapor fraction is separated based upon boiling point into at least (a) an overhead fraction containing methyl iodide, water, methanol, methyl acetate, acetic acid, alkanes and acetaldehyde and (b) an acetic acid stream containing acetic acid, water, hydrogen iodide and heavy impurities such as propionic acid.

In a decanter, the overhead fraction is condensed and separated by density to (a) a lighter aqueous phase and (b) a heavier organic phase. The lighter aqueous phase can contain water, acetic acid, methyl acetate, methyl iodide, acetaldehyde and alkanes and have a density of about 1.0 grams per cubic centimeter to about 1.10 grams per cubic centimeter. Like the lighter aqueous phase, the heavier organic phase can contain water, acetic acid, methyl acetate, methyl iodide, acetaldehyde and alkanes; the organic phase may further comprise higher concentrations of methyl iodide and alkanes. The heavier organic phase can have a density of about 1.4 grams per cubic centimeter to about 2.2 grams per cubic centimeter. The lighter aqueous phase can be recycled to the reactor or to the light ends distillation column.

In a drying column, the residual water is removed from the acetic acid stream. In a heavy ends distillation column, the heavy impurities are removed from the acetic acid stream.

In some embodiments, a method for measuring the various acetic acid stream components is performed using an online infrared spectroscopy method. The concentration measurements are used to adjust the reaction system, while an attenuated total reflectance (ATR) probe can be used to monitor a reactor's solution. A light signal can be transferred to a detector by light pipe, chalcogenide fiber or other methods. Alternatively, a reactor slipstream can pass through an infrared analyzer equipped with a flow-through ATR cell or flow-through transmission cell. Continuous flow can be employed, and the reactor solution can be returned to the reaction system. The use of a back pressure regulator or similar device can prevent a pressure drop across the cells, thereby ensuring analyses are performed with minimal change from the reactor pressure and there is no degassing or bubble formation in the cells.

The temperature of the slipstream can be maintained anywhere between ambient and process temperature. Selection of the temperature depends on several parameters, such as precipitation of solids, compatibility of the cell window or crystal materials with process conditions and controlling the process reaction in the slipstream.

Depending on the temperature employed, the cell window or crystal material can be selected from the group consisting of $CaF_2$, ZnS, sapphire, AMTIR (Se—Ge—As composite), Ge, ZnSe, Si, diamond, KRS-5 (thallium bromoiodide) and cubic zirconia. While in no way limiting the scope of the technology, sapphire is desirable in some embodiments because it has the appropriate transmission range to allow certain analyses to be performed and displays good mechanical strength, chemical resistance and resistance to etching in the process.

All tubing, valving and the like contacting the reaction solution must be chemically inert to the reaction components and be capable of withstanding corrosive attack under reaction conditions. Suitable manufacturing materials for use in the tubes, valves, and similar equipment include HASTELLOY™ B2 Ni—Mo—Fe alloy, HASTELLOY™ B3 Ni—Mo—Fe alloy and zirconium.

The monitoring of the acetic acid reaction components in accordance with the present technology can be carried out by analyzing a combination of select spectral ranges of traditional mid (400-4000 $cm^{-1}$) and extended mid (4000-7000 $cm^{-1}$) infrared (IR) regions. Infrared spectroscopy can measure rhodium, dissolved carbon dioxide, water, acetic acid, hydrogen iodide, methyl iodide, methyl acetate and triphenyl phosphine oxide.

One option for monitoring the acetic acid reaction components involves the use of a dual transmission cell, dual detector setup in which the reactor solution sequentially flows through both cells. These cells differ only in path length. In some embodiments, one cell may have a path length of 0.05-0.15 mm, which allows for analysis in the spectral region between 1800-5600 $cm^{-1}$ and thereby encompasses portions of traditional mid- and extended mid-infrared regions. The second cell, in certain embodiments, may have a path length of 0.2-3.0 mm, which allows for analysis only in the extended mid-infrared region. The different cell path lengths can be utilized to counteract the highly absorbing nature of acetic acid and take advantage of the two different spectroscopic regions for reactant component characterization.

Alternatively, a single transmission cell and single detector setup can be used. For example, a cell with a path length of 0.05-0.15 mm can be used for the "non-fingerprint" region (i.e., 1800-5600 $cm^{-1}$). Another possible cell may have, in some embodiments, a much shorter path length of 0.005-0.015 mm, which allows for coverage of both the non-fingerprint region and the fingerprint region (i.e., 1800-400 $cm^{-1}$). This shorter path length can also be effectively achieved by using an attenuated total reflectance (ATR) crystal rather than a transmission cell.

Drawbacks regarding the use of infrared spectroscopy include large $H_2O$ absorbance values, large acetic acid absorbance values, relatively weak methyl iodide absorbance values, and the tendency of $H_2O$ and acetic acid absorbance values to overlap and interfere with the absorbance of other components. As such, calibration for methyl iodide and methyl acetate is difficult to achieve and may adversely affect quantitation of detectable species.

Additionally, a large number of calibration standards are required for acetic acid processes to obtain calibration models with acceptable accuracy. Moreover, infrared spectroscopy has drawbacks regarding hardware flexibility and implementation in a process environment.

A method for measuring the various components is online Raman spectroscopy. Like the infrared method, this Raman method provides concentration measurements that can be used to adjust the reaction system. A Raman shift occurs when light impinges upon a molecule and interacts with the electron cloud and the bonds of that molecule. It is believed that a photon excites the molecule from the ground state to a virtual energy state and that when the molecule relaxes, the molecule emits a photon and returns to a different rotational or vibrational state. The difference in energy between the original state and the new state leads to a shift in the emitted photon's frequency away from the excitation wavelength. Raman spectra can be shown as plots of intensity (arbitrary units) versus Raman shift. Raman shifts can be expressed in wavenumbers, which have units of inverse length such as inverse centimeters ($cm^{-1}$).

The instrumentation used to collect and process Raman data includes a Raman spectrometer system, a transmittance system, a control loop and a processor. The Raman spectrometer system comprises a Raman spectrometer, with its principal components being a light source, a monochromator and a detector. The light source delivers excitation radiation to the probe, where scattered radiation is collected, filtered of Raleigh scattered light and dispersed via a monochromator. The dispersed Raman scattered light is then imaged onto a detector and subsequently processed within the processor.

The light source can be a visible laser, such as a frequency-doubled Nd:YAG laser (532 nm), a helium-neon laser (633 nm) or a solid-state diode laser (785 nm). The laser can be pulsed or continuous wave (CW), polarized as desired or randomly polarized, or single-mode. Light sources other than lasers can be used. The excitation radiation can be delivered to the probe, and the scattered radiation can be collected from the probe.

The scattered radiation of the carbonylation reaction mixture may be collected by a probe in a variety of locations in one or more of the separations units. The probe may be placed directly in a vessel, a feed stream entering or exiting the unit or a slip stream. Alternatively, the probe may be situated such as not to contact a liquid mixture. An issue with Raman probes is that their external crystal structures can become coated over time with the chemicals that are probed. The coating of the cell window or the probe crystal will lead to a decrease in signal reaching the detector, with an associated decrease in measured component concentration values. As such, the coating can significantly impact the accuracy of the probes and impede process control.

Infrared spectroscopy is not similarly affected. In the presence of a coating, infrared spectroscopy can maintain sufficient signal strength beyond the point when a similarly-coated Raman probe is no longer useful for providing data for quantitative analysis. For online process measurement, fiber optic cables can be used to deliver the excitation radiation and collect the scattered radiation. The use of fiber optic cables facilitates positioning the excitation source remotely from the sampling region, providing an environmental advantage for Raman spectroscopy over infrared systems.

The collected scattered radiation is filtered to remove Raleigh scattering and frequency (wavelength) dispersed using a suitable dispersive element or interferometrically. The monochromator can be any such dispersive element, along with associated filters and beam manipulation optics. The dispersed Raman scattering is imaged onto a detector. Detectors can include array detectors or single element detectors. In the case of array detectors, the detector is calibrated such that the frequency (wavelength) corresponding to each detector element is known. The detector response is delivered to the processor that generates a set of frequency shift, intensity (x,y) data points which constitute the Raman spectrum. Raman spectroscopy can measure water, acetic acid, hydrogen iodide, methyl iodide, methyl acetate, acetaldehyde, triphenyl phosphine oxide and dissolved carbon monoxide.

In a general embodiment, the present disclosure provides a method for measuring the concentration of one or more components in the reactor or a separation unit of the acetic acid process by both infrared and Raman spectroscopic analyses and then adjusting the conditions in the reactor or in any subsequent step of the acetic acid production process in response to the measured concentration. As previously-noted, infrared spectroscopy can measure rhodium, dissolved carbon dioxide, water, acetic acid, hydrogen iodide, methyl iodide, methyl acetate, and triphenyl phosphine oxide, while Raman spectroscopy can measure water, acetic acid, hydrogen iodide, methyl iodide, methyl acetate, acetaldehyde, triphenyl phosphine oxide and dissolved carbon monoxide.

Examples of condition adjustments include increasing or decreasing the temperature or the pressure of the reactor or separation unit(s). Additionally, the flow rates of the feeds or exit streams can be increased or decreased. Such adjustments can affect the concentrations of one or more components in the reactor or a separations unit to bring the components within a desired range. Notably, the concentration of methyl iodide and the catalyst can determine the reaction rate. The concentration of the triphenyl phosphine oxide affects catalyst stability and reaction rate. The concentration of methyl acetate indicates the percentage of catalyst being used for carbonylation (i.e., the amount of idle catalyst). The amount of water is necessary for ensuring formation of acetic acid, as water is used in the final step of the catalytic process. The dissolved carbon monoxide assists in catalyst regeneration and indicates the by-product water-gas-shift reaction.

The present disclosure allows for certain additives such as triphenyl phosphine oxide (TPPO) to be measured accurately by infrared spectroscopy without any of the interference described in reference to water, acetic acid, methyl iodide and methyl acetate. Moreover, Raman spectroscopy permits for the calibration of accurate methyl iodide and methyl acetate concentration predictions. Notably, methyl iodide has a strongly-scattering, characteristic peak in the Raman spectrum, with imperceptibly low interference from any other reactor solution components. Additionally, water and acetic acid Raman peaks permit accurate measurement of their concentrations without interfering with peaks for methyl iodide or methyl acetate. In addition, TPPO can also be accurately measured by Raman spectroscopy.

As previously noted, an issue with Raman probes is that their external crystal structures can become coated over time. The coating of the cell window or the probe crystal will lead to a decrease in signal reaching the detector and an associated decrease in measured component concentration values. As such, the coating can significantly impact the accuracy of the probes and impede process control. The present disclosure provides that the detrimental effect of Raman probe coating on the accuracy of measurements can be corrected by correlating infrared measurements of certain components to measurements obtained when the Raman probe was uncoated. Examples of the components include TPPO and acetic acid.

The present disclosure provides for a method for using the ratio (Adjustment Ratio) of (a) for the infrared measurement for a reference component measurable by infrared and Raman spectroscopic methods (Reference$_{infrared}$) and (b) the Raman measurement obtained for the reference component (Reference$_{Raman}$), to adjust the Raman values for all measured components (Component$_{Adjusted}$). This ratio-based adjustment permits accurate measurement of components that are more easily measured by Raman spectroscopy than infrared spectroscopy, such as methyl iodide, methyl acetate and dissolved carbon monoxide (Component$_{Raman}$).

$$Component_{Adjusted} = (Reference_{infrared} / Reference_{Raman}) * Component_{Raman}$$

In a particular embodiment, the method can be performed instantly or in real time. In a general embodiment, the present disclosure provides for a method for the production of acetic acid containing the steps of:
(A) reacting, in a carbonylation reactor and the presence of a carbonylation catalyst:
  (i) methanol,
  (ii) carbon monoxide, and
  (iii) water,
  to produce a reactor mixture;
(B) measuring the concentration of a reference component and a second component in the reactor mixture by both infrared and Raman spectroscopic analyses;
(C) determining the ratio (Adjustment Ratio) of the concentration of the reference component as measured by infrared spectroscopy to the concentration as measured by Raman spectroscopy;
(D) calculating the adjusted value (Adjusted Value) for the second component by multiplying the concentration of the second component as measured by Raman spectroscopy by the Adjustment Ratio; and
(E) modifying a process condition in the carbonylation reactor or a separation unit, based upon the Adjusted Value.

The ingredients can further include methyl acetate, a catalyst stabilizer, a catalyst promoter and/or hydrogen iodide. As previously-noted, there are two types of catalyst stabilizers in general. The first type of catalyst stabilizer is metal iodide salt such as lithium iodide. The second type of catalyst stabilizer is a non-salt stabilizer, including pentavalent Group VA oxides such as phosphine oxides. An example of a catalyst promoter is methyl iodide. Methyl iodide may be added directly to the process or generated by adding hydrogen iodide to the process. The reactor mixture can include the carbonylation catalyst, methanol, methyl acetate, water, carbon monoxide, carbon dioxide, methyl iodide, or acetic acid.

In some embodiments, the Raman probe can become sufficiently coated as to render inappropriate any further use of an Adjustment Ratio to calculate an Adjusted Value. The situation may arise when the probe has a signal of 20% or less. As such, when the Adjustment Ratio is about 5 or greater, the Raman probe should be cleaned. In some embodiments, the Adjustment Ratio is has a value of less than about 5. In some embodiments, the Adjustment Ratio is has a value of 0.01 to about 5. Examples of process conditions that can be modified include the temperature of the carbonylation reactor, the pressure of the carbonylation reactor, a temperature of a separation unit, a pressure of a separation unit, a flow rate of an ingredient, a flow rate of an exit stream, the concentration of a component, and the selection of a component.

EXAMPLES

The following example is included to demonstrate certain embodiments of the technology. It should be appreciated by those of skill in the art that many changes can be made in the specific embodiments described herein and still obtain similar results without departing from the spirit and scope of the disclosure.

Data in this example were obtained from a continuous methanol carbonylation unit equipped with a reactor, a flash tank, a light ends distillation column, a decanter, a drying column and two flow-through cells. A reactor slipstream was continuously passed in series through the flow-through cells and returned to the process via the flash tank. The flow-through cells were maintained at about the temperature and the pressure of the reactor, which were about 175° C. and 400 psig (2760 kPa), respectively.

The first flow-through cell contained a Kaiser Optical Systems fiber optically coupled Raman probe with a sapphire crystal, while the second flow-through cell contained a Mettler Toledo optical conduit coupled 9 bounce ATR infrared probe with a silicon crystal. The parts of both probes that were in contact with the process solution were constructed of HASTELLOY™ B2 alloy.

The example pertains to a time period of about 8 hours of continuous operation during which the Raman probe became heavily coated with solid material. The process solution contained components present in a methanol carbonylation process such as water, methyl acetate, rhodium catalyst, triphenyl phosphine oxide, acetic acid and methyl iodide.

The trend lines in FIG. 1 show that acetic acid (HOAc) and TPPO concentrations, as determined by both Raman and infrared measurement, agree closely for the first few hours of the time period. Subsequently, Raman TPPO and HOAc measured concentrations decrease significantly. The corresponding infrared measured concentrations remained essentially invariant. FIG. 1 also shows a decrease in Raman measurements for MeI.

Figure 2:
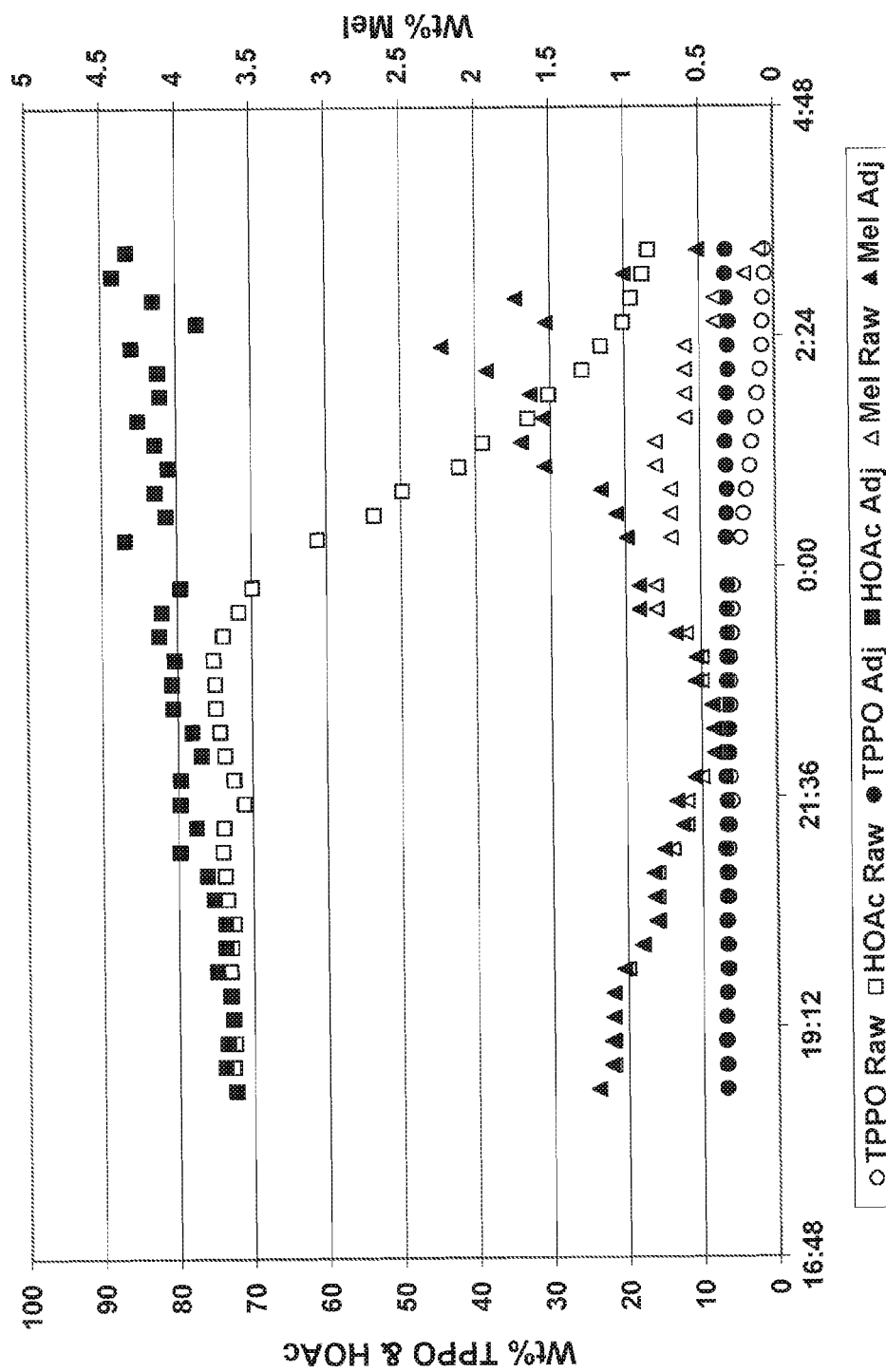
FIG. 2 is a graph showing time-lapse measurements of certain components in a methyl carbonylation process from FIG. 1 with adjusted measurements for those components overlaid on that graph.

In FIG. 2, the raw Raman measurements from FIG. 1 are re-plotted along with their corresponding adjusted values. The adjusted values were obtained by taking each instantaneous TPPO concentration as measured by infrared, dividing this value by each instantaneous TPPO concentration as measured by Raman, and then multiplying the raw Raman concentration values of HOAc and MeI by the result of each instantaneous infrared TPPO/Raman TPPO ratio.

$$HOAc_{Adjusted} = (TPPO_{infrared}/TPPO_{Raman}) * HOAc_{Raman}$$

$$MeI_{Adjusted} = (TPPO_{infrared}/TPPO_{Raman}) * MeI_{Raman}$$

Table 1 shows data based upon samples collected at about the 7$^{th}$ hour of an 8-hour operation. One sample was analyzed online via the flow-through cells, and the other sample was collected from the reactor for offline analysis by IR and gas chromatography.

The raw Raman value of each component was multiplied by 3.7, which corresponds to the TPPO$_{infrared}$/TPPO$_{Raman}$ ratio. The conversion was validated by the offline analysis of a sample removed from the reactor at the same time. The validity of TPPO was confirmed through an offline IR analysis. The validity of the adjusted values for MeI and HOAc were confirmed through an offline gas chromatography analysis, as MeI cannot be reliably evaluated using IR spectroscopy.

TABLE 1

| Component | Raman$_{Raw}$ | Infrared | Raman$_{Adjusted}$ | Offline Measurement |
|---|---|---|---|---|
| Triphenyl Phosphine Oxide | 1.7 | 6.3 | 6.3 | 6.5 |
| Acetic acid | 23.2 | 84.8 | 86.8 | 78.2 |
| Methyl iodide | 0.6 |  | 2.2 | 2.5 |

Although the present technology and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods and/or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods and/or steps.

What is claimed is:

1. A method for the production of acetic acid comprising:
   i. reacting, in a carbonylation reactor and the presence of a carbonylation catalyst, ingredients comprising:
      (i) methanol,
      (ii) carbon monoxide, and
      (iii) water,
      to produce a reactor mixture;
   ii. measuring the concentration of a reference component and a second component in the reactor mixture by both infrared and Raman spectroscopic analyses;
   iii. determining the Adjusted Ratio of the concentration of the reference component as measured by infrared spectroscopy to the concentration as measured by Raman spectroscopy;
   iv. calculating the Adjusted Value for the second component by multiplying the concentration of the second component as measured by Raman spectroscopy by the Adjustment Ratio; and
   v. modifying a process condition in the carbonylation reactor or a separation unit, based upon the Adjusted Value.

2. The method of claim 1, wherein the ingredients further comprise methyl acetate.

3. The method of claim 1, wherein the ingredients further comprise a catalyst stabilizer.

4. The method of claim 1, wherein the ingredients further comprise a catalyst promoter.

5. The method of claim 4, wherein the catalyst promoter is methyl iodide.

6. The method of claim 5, wherein the reactor mixture comprises:
   i. the carbonylation catalyst;
   ii. methanol;
   iii. methyl acetate;
   iv. water;
   v. carbon monoxide;
   vi. carbon dioxide;
   vii. methyl iodide; and
   viii. acetic acid.

7. The method of claim 1, wherein the ingredients further comprise hydrogen iodide.

8. The method of claim 7, wherein the reactor mixture comprises:
   i. the carbonylation catalyst;
   ii. methanol;
   iii. methyl acetate;
   iv. water;
   v. carbon monoxide;
   vi. carbon dioxide;
   vii. methyl iodide; and
   viii. acetic acid.

9. The method of claim 1, wherein the Adjustment Ratio is less than 5.

10. The method of claim 1, wherein the process condition comprises:
    i. the temperature of the carbonylation reactor;
    ii. the pressure of the carbonylation reactor;
    iii. a temperature of a separation unit;
    iv. a pressure of a separation unit;
    v. a flow rate of an ingredient;
    vi. a flow rate of an exit stream;
    vii. the concentration of a component; and
    viii. the selection of a component.

* * * * *

UNITED STATES PATENT AND TRADEMARK OFFICE
CERTIFICATE OF CORRECTION

PATENT NO. : 9,656,939 B2  
APPLICATION NO. : 15/062756  
DATED : May 23, 2017  
INVENTOR(S) : Noel C. Hallinan et al.

Page 1 of 1

It is certified that error appears in the above-identified patent and that said Letters Patent is hereby corrected as shown below:

In the Specification

Column 9    Line 20    Delete "$HOAC_{Adjusted}=(TPPO_{infrared}/TPPO_{Raman})*HOAC_{Raman}$" and insert --$HOAc_{Adjusted}=(TPPO_{infrared}/TPPO_{Raman})*HOAc_{Raman}$--

Signed and Sealed this  
Twenty-eighth Day of January, 2020

Andrei Iancu  
*Director of the United States Patent and Trademark Office*